United States Patent [19]

Ozick

[11] Patent Number: 5,188,817
[45] Date of Patent: Feb. 23, 1993

[54] METHOD OF TREATMENT FOR PERIODONTITIS

[76] Inventor: Julius Ozick, 2 Parkview Ave., New Rochelle, N.Y. 10805

[21] Appl. No.: 575,854

[22] Filed: Aug. 31, 1990

Related U.S. Application Data

[63] Continuation-in-part of Ser. No. 329,342, Mar. 27, 1989, abandoned.

[51] Int. Cl.$^5$ .......................... A61K 7/16; A61K 9/68; A61K 31/07
[52] U.S. Cl. ........................................ 424/49; 424/48; 424/435; 424/440; 424/447; 514/570; 514/900; 514/902
[58] Field of Search ................. 514/570, 900, 902; 424/49-58

[56] References Cited

U.S. PATENT DOCUMENTS

| | | | |
|---|---|---|---|
| 3,992,519 | 11/1976 | Hofmann et al. | 424/48 |
| 4,405,610 | 9/1983 | Krnjevic | 424/180 |
| 4,861,582 | 8/1989 | Pollock et al. | 424/520 |
| 4,889,720 | 12/1989 | Konishi | 424/448 |
| 4,971,785 | 11/1990 | Wilson et al. | 424/44 |
| 4,985,235 | 1/1991 | Kligman | 514/49 |
| 5,009,886 | 4/1991 | Ahmed et al. | 424/58 |
| 5,032,384 | 7/1991 | Yeh et al. | 424/49 |

FOREIGN PATENT DOCUMENTS

| | | |
|---|---|---|
| 353675 | 7/1989 | European Pat. Off. |
| 380367 | 1/1990 | European Pat. Off. |
| 1514469 | 6/1978 | United Kingdom |

OTHER PUBLICATIONS

Varova GA. 101 #157642h (1983).
Trykowski CA 113#11920C (1990).
Hong, et al., *New Eng. J. Med.*, 315:1501–1505 (1986).
Kock, *J. Max-Fac. Surg.*, 6:59–63 (1978).
Handler, *J. Am. Acad. Dermatol.*, 10:674 (1984).

*Primary Examiner*—Shep K. Rose
*Attorney, Agent, or Firm*—Bryan Cave

[57] ABSTRACT

A method of treatment for periodontitis comprises the topical or systemic administration of a pharmaceutical composition containing at least one retinoid compound other than Vitamin A. Preferred retinoids include Vitamin A aldehyde, Vitamin A acid, Vitamin A esters, isotretinoin, etretinate and acitretin.

11 Claims, 2 Drawing Sheets

METHOD OF TREATMENT FOR PERIODONTITIS

CROSS-REFERENCE TO RELATED APPLICATION

This application is a continuation-in-part of copending application Ser. No. 07/329,342, filed Mar. 27, 1989, now abandoned.

BACKGROUND OF THE INVENTION

1. Field of the Invention

The invention relates to methods of treating periodontal disease.

2. Description of the Prior Art

The term "periodontal disease" actually encompasses a number of diseases that affect the supporting tissues of the teeth. The periodontium consists of the investing and supporting tissues of the tooth, and consists of the gingiva, the periodontal ligament, the cementum and the alveolar bone. The periodontium is subject to morphological and functional variations, to changes associated with age and to pathology.

The term gingivitis refers to an inflammation of the gingival tissue. Recent research on periodontal disease shows that not all patients with gingivitis progress to periodontal disease. However, gingivitis may be the first sign of oncoming periodontal disease and most, if not all, periodontal disease has an accompanying gingivitis.

Periodontitis is defined as inflammation involving the gingival unit (gingiva and alveolar mucosa) and extends to the periodontal ligament, alveolar bone, and cementum. Periodontitis involves loss of clinical attachment and radiographic loss of bone. The conversion clinically from gingivitis to periodontitis reflects the progression, histopathologically, from the established stage to the advanced stage of the periodontal lesion.

The vast body of evidence indicates that the primary cause of both gingivitis and periodontitis is bacterial activity. Bacteria attach to the tooth surface at and slightly under the gingival margin. They colonize and form an organized mass that is referred to as bacterial plaque. This plaque, if allowed to remain, brings about inflammatory changes in the tissues. The pathogenic potential of plaque can vary from one individual to another and from tooth to tooth within an individual. The reaction of the host tissues to this bacterial attack is through an inflammatory and immunologic defense mechanism.

Prophylactic measures to maintain good oral hygiene and keep teeth and gums in a relatively plaque-free state are important in the prevention of most treatable forms of periodontal disease. The patient's own brushing, flossing and utilization of certain antiseptic mouthwashes which may be of value in controlling plaque are supplemented by professional scaling and root planing treatments.

Once active periodontitis develops, however, a variety of treatment modalities have been utilized to combat the disease and prevent its progression. These include periodontal surgery: e.g., curettage, givgivectomy, flap or pocket elimination and the modified Widman flap procedure; and chemotherapy, particularly local and systemic antibiotic treatment. The antibiotic agents most frequently used are the tetracyclines and metronidazole. Excellent reviews of current knowledge regarding periodontal disease in general and periodontitis in particular, as well as conventional treatment methods, include V. J. Iacono, *NYS Dent. J.*, 53:24–29 (1987); T. J. O'Leary et al., *J. Periodont.*, 59:306–310 (1988); L. Saxen, *Int. Dent. J.*, 35:291–296 (1985); W. C. Hurt et al., *Baylor Dent. J.*, 32:17–19 (1988).

The conventional methods currently utilized to treat periodontal disease suffer from a number of significant drawbacks. Surgical reduction of periodontal pockets can expose roots, cause sensitivity, and result in poor esthetics by a lengthening of the clinical crown and altering the gingival contours. Surgical treatment does not guarantee that the disease process will not recur to the detriment of the patient's dentition.

Antibiotic therapy is not usually totally successful, particularly in advanced cases, probably because the site of action of periodontal disease is not accessible to a sufficient concentration of drug at the base of the periodontal pocket to completely halt the disease process. Anti-microbial solutions have been introduced through irrigating devices to the periodontal pocket with some success, but are not curative. Sustained systemic administration of antibiotics such as tetracyclines is inadvisable because of the potentially serious side effects and the possibility of giving rise to antibiotic-resistant infections.

New, more effective approaches to the treatment of periodontal disease, particularly periodontitis, are actively being sought.

SUMMARY OF THE INVENTION

It is the object of the present invention to provide a method of treatment for periodontitis which overcomes the aforementioned drawbacks of prior art methods and may be practiced by patients at home as well as utilized by professional dental practitioners. In keeping with this object, and others that will become apparent hereinafter, the present invention resides in the administration to patients suffering from periodontitis of non-toxic, therapeutic amounts of Vitamin A derivatives or analogs, hereinafter collectively referred to as "retinoids", but not Vitamin A itself. The retinoids may be administered systemically or by topical application at the disease site.

Any of a variety of conventionally available, orally acceptable retinoid preparations can be utilized for systemic therapy, as well as any other pharmaceutically acceptable preparation containing one or more retinoids as its active ingredient together with an inert carrier or vehicle. The retinoids can be applied locally to the affected periodontal tissue area in a cream, gel or ointment vehicle, by injection into the periodontal pocket, through the use of irrigating devices fitted with blunt hypodermic needles, by the application of retinoid-containing patches to the disease site, or by any other conventional method for effectively bringing and maintaining a topical pharmaceutical agent in contact with its tissue site of action.

DETAILED DESCRIPTION OF THE INVENTION

Figure 1:
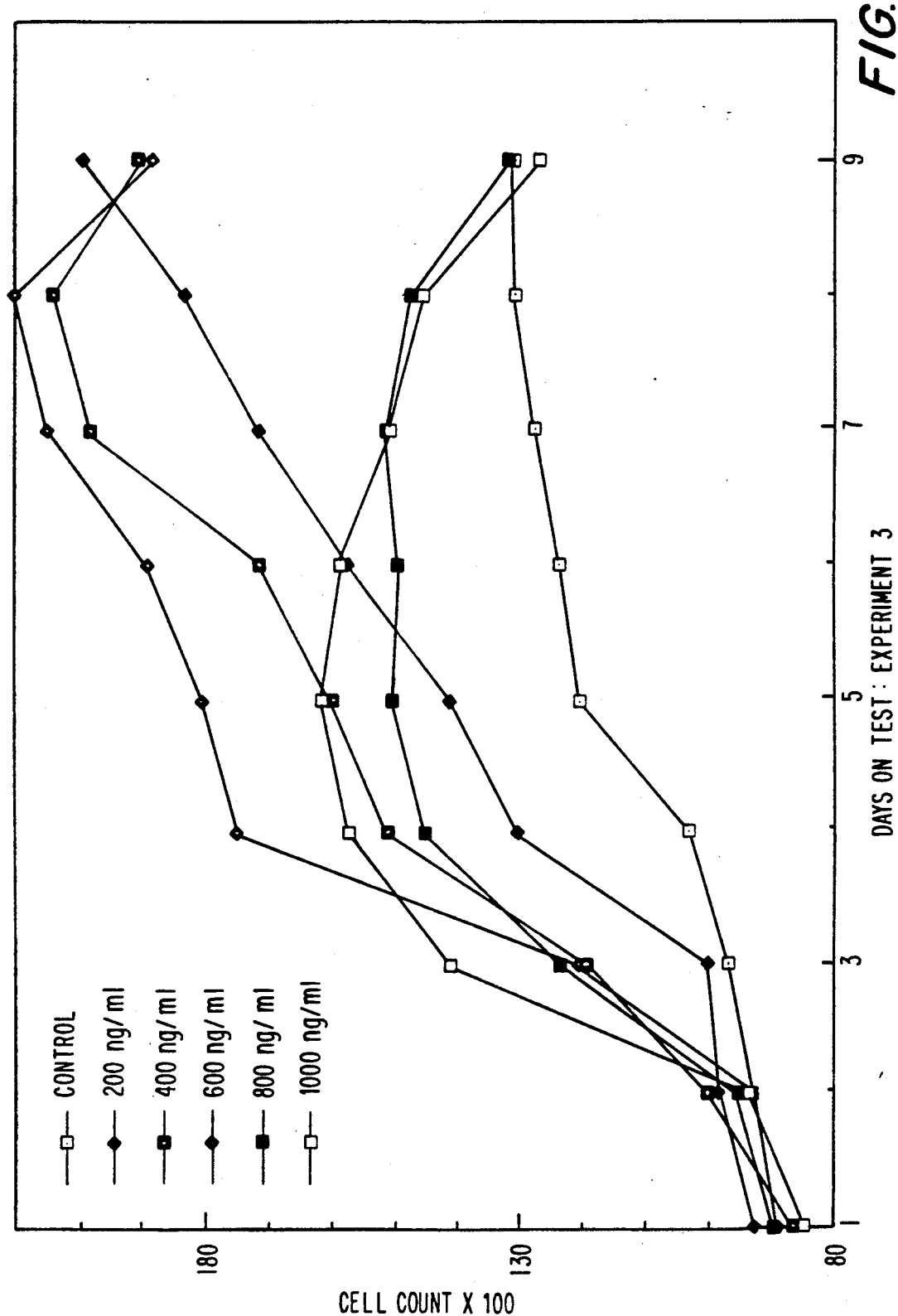
FIG. 1 is a graph showing the number of human gingival fibroblasts counted in six wells of a cell culture plate at one-day intervals over a period of nine days, each of the wells containing either a specified concentration (from 200 to 1000 ng/ml) of isotretinoin dissolved in culture medium, or none at all (control).

The present invention deals with a conceptual change in approach to the treatment of periodontal disease. Rather than attempting to eradicate or suppress the growth of the literally hundreds of microbial species found in the mouth, and particularly in plaque, the novel method is directed to treating the target tissues of the host (the periodontal tissues) so as to render them less susceptible and more resistant to the pathological effects of the microbial population.

Accordingly, the present invention resides in the administration to a patient suffering from periodontitis of a topical or systemic pharmaceutical composition comprising as its active ingredient an effective periodontal tissue protective amount of at least one retinoid compound other than Vitamin A. Preferred retinoids for use in the present invention include:

Vitamin A aldehyde (retinal, retinene)
Vitamin A acid (tretinoin, retinoic acid)
Vitamin A esters (e.g., retinyl palmitate)
isotretinoin
etretinate
acitretin (free acid of etretinate)

The structures of the preferred retinoids are shown below:

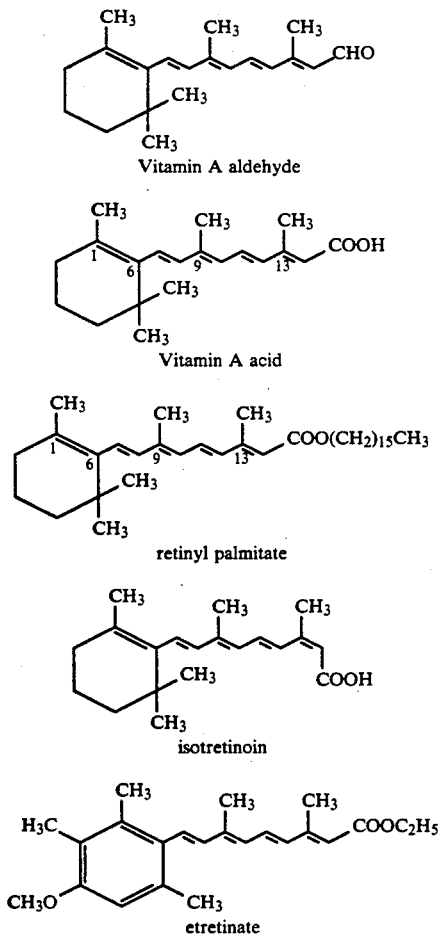

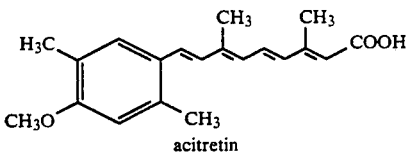

acitretin

A number of the preferred retinoids specified above are commercially available in approved oral or topical preparations: for example, Accutane (isotretinoin) and Tegison (etretinate) capsules from Roche Laboratories, Nutley, N.J.; Retin-A (tretinoin) cream from Ortho Pharmaceutical Corp., Raritan, N.J.; and numerous oral and topical compositions containing Vitamin A derivatives.

Vitamin A (retinol), whether in topical or systemic dosage form, may not be used in the practice of the present invention. It has been clearly documented in the literature that prolonged systemic administration of Vitamin A in therapeutic doses (e.g., in excess of 100,000 I.U. daily) frequently leads to hypervitaminosis A, with potentially life-threatening complications. See, e.g., *J. Am. Dent. Assoc.*, Report of Council on Dental Therapeutics, Vol. 61, July 1960, pp. 142-143 (prolonged Vitamin A therapy for oral keratotic lesions to be discouraged); E. V. Zegarelli et al., *NYS Dent. J.*, Vol. 25, June-July 1959, pp. 244-252 (to obtain desired clinical results in leukoplakia and lichen planus therapy with Vitamin A, it is necessary to administer essentially toxic doses). Moreover, even when Vitamin A is applied topically to the gingiva or other oral mucosa in therapeutic dosages, absorption into the systemic circulation occurs at high levels and toxic effects may be observed. See Zegarelli et al., supra, at 251; S. Silverman et al., *J. Oral Ther. Pharm.*, Vol. 2, No. 1, 1965, pp. 9-23 (patients treated for leukoplakia with Vitamin A troches dissolved in the mouth showed toxic effects, including altered liver function). Topical application of Vitamin A may also cause local tissue damage. C. J. Cavalaris et al., *J. Oral Ther. Pharm.*, Vol. 3, No. 6, 1967, pp. 452-461 (continuous application of Vitamin A to hamster cheek pouch caused tissue alterations and ultimately mucous metaplasia).

While Vitamin A itself is not useful in treating periodontal disease, either systemically or topically, synthetic retinoid analogs of Vitamin A are effective in retarding gingivitis and other manifestations of periodontal disease, without the need for administering toxic dosage levels. The usefulness of the synthetic retinoids may lie in the fact that they are probably not bound in vivo by retinol bonding protein (as is Vitamin A) and thus may exert a therapeutic effect in amounts far below those which may be considered toxic. See, e.g., C. H. Dicken, *J. Am. Acad. Derm.*, Vol. 11, No. 4, October 1984, pp. 541-552 (retinoids such as 'isotretinoin and etretinate bind to albumin and/or plasma lipoproteins, not retinol bonding protein); B. A. Pawson, *J. Am. Acad. Derm.*, Vol. 6, No. 4, April 1982, pp. 577-582 (synthetic retinoids less toxic than Vitamin A).

Vitamin A has only been employed in the treatment of conditions related to periodontal disease as one ingredient in experimental topical formulations, the other ingredients having a tendency to mitigate the toxicity of the Vitamin A and/or to provide different therapeutic actions. For example, in Skylar et al., Russian Pat. No. 950387, a toothpaste is disclosed containing a series of ingredients including Vitamin A and Vitamin E. The latter is believed to protect against hypervitaminosis A—see Goodman and Gilman, *The Pharmacological Basis of Therapeutics*, 7th ed., at p. 1577.

In Khmelevski et al., *Vopr. Pitan.*, pp. 54–56 (July-Aug. 1985), a topical composition is disclosed for use in certain oral therapies which contains an emulsion of Vitamin A, an emulsion of Vitamin E (again, probably to counteract the toxicity of the former) and an emulsion of Vitamin K.

There has been no prior disclosure of use of low toxicity analogs of Vitamin A as effective periodontal disease-alleviating active ingredients, either in systemically or topically administered form. These compounds have been used to reverse dysplasia of oral leukoplakia (a pre-cancerous condition) and lichen planus. See C. H. Dicken, *J. Am. Acad. Derm.*, Vol. 11, No. 4, Part II, p.548 (1984). Both lichen planus and leukoplakia are conditions unrelated in etiology and symptomatology to periodontitis.

A preferred daily dosage range for retinoids administered orally (i.e., systemically by the oral route) to treat periodontitis in accordance with the present invention is from about 0.1 to about 5.0 mg/kg of body weight, typically given over a period of from about 10 to about 20 weeks as an initial course of treatment. A more preferred dosage range is from about 0.5 to about 2.0 mg/kg daily. The daily dosage can be administered in one to four equally divided doses.

The preferred concentration range of retinoids in topical preparations used in the methods of the present invention is from about 0.01 to about 0.1% by weight, with a more preferred range of about 0.025 to about 0.05%. The exact concentration depends greatly upon the delivery method and topical vehicle chosen, which in turn affects the amount of drug available to the periodontal tissues.

Suitable oral preparations for use in the methods of the present invention include any conventional oral pharmaceutical dosage forms (e.g., capsules, tablets, caplets, liquids, suspensions, lozenges, and the like) containing as their active ingredients one or more retinoid compounds, preferably in such amount that one to four dosage units will comprise a daily oral dosage of retinoids coming within the range set forth above. These oral dosage forms may include any conventional vehicles, carriers, excepients, binders, flavoring agents and other suitable inactive ingredients known to those skilled in the pharmaceutical arts. Moreover, the oral dosage forms may comprise active ingredients in addition to the retinoid compounds, e.g., orally effective antibiotics or other agents useful in the treatment of periodontitis or its sequelae.

Topical compositions for local treatment of affected periodontal tissues may include conventional creams, ointments, pastes and gels containing Vitamin A esters and other retinoid derivatives, to the extent that those products may be safe and acceptable for oral use in terms of toxicity, taste and consistency. In general, any topical vehicle compatible with the retinoids and acceptable for use in the mouth may be used in formulating topical compositions for practicing the novel treatment methods. Particularly suitable vehicles are topical dental pastes of the type commonly utilized for oral corticosteroid compositions, e.g., Orabase (Colgate-Hoyt Laboratories, Caton, Mass.), and anhydrous ointment bases such as Aquaphor (Beiersdorf Inc., Norwalk, Conn.).

Topical treatment with retinoids may also be provided through the use of irrigation devices associated with blunt hypodermic needles inserted in the periodontal crevices, with orally acceptable solutions of the retinoids used in the irrigation reservoir. Slow release patches containing retinoids may also be applied to the gingivae, similar to patches currently utilized for transdermal administration of nitroglycerin and other cardiovascular treatment agents.

Emulsions of retinoids in sticky vehicles, such as gum arabic, may be formulated and adhered to the affected tissues, or made into chewing gum to provide a sustained release of treatment agent. Similarly, the retinoid compounds can be dissolved in food grade plastic made into thin filaments to be inserted in the gingival crevices. This method has been suggested with respect to tetracycline therapy. Therapeutic toothpastes or gels can also be provided containing retinoids for regular hygienic use by patients.

Where higher tissue concentrations of the retinoids are deemed necessary to provide effective therapy to the affected periodontal tissues, sterile parenteral solutions of one or more retinoids may be injected directly into the gingivae. Such solutions may be prepared with any conventional injectable vehicles for oral use in which the retinoids are soluble.

In general, any systemic or local methods of administration capable of providing effective therapeutic amounts of the active retinoid agents to achieve the goal of protecting the periodontal tissues from microbial assault may be utilized in practicing the method of the present invention.

Treatment of periodontal tissues with retinoids in accordance with the methods of the invention renders the tissues less susceptible to the pathological effects of periodontal bacteria, particularly the cytopathic species which cause greatest tissue degeneration. These treatment methods may be practiced prophylactically in patients prone to periodontitis or to treat mild, moderate or advanced cases of the disease. Beneficial results can generally be expected within the first ten to twenty-week course of treatment, and treatment can be renewed if regression occurs following the first course.

The following example, setting forth the results of an in vitro study, provides evidence that the method of the present invention is efficacious. The example is illustrative and is not intended to restrict the scope of the invention in any way.

EXAMPLE

Effects of Retinoids on Human Gingival Fibroblasts

Summary

Two retinoids, isotretinoin and acitretin, each at concentrations of 200, 400, 600, 800 and 1,000 ng/ml, were tested on human gingival fibroblasts cultured in vitro. After nine days on test, all five retinoid concentrations for both isotretinoin and acitretin induced increased fibroblast population growth. After the fifth day, the two higher levels of both retinoids showed lessened growth and a trend returning toward the normal growth curve. In these two retinoid levels, dead and dying cells were noted in the cell culture wells. These results suggest that both isotretinoin and acitretin at concentrations less than 600 ng/ml stimulate the population growth of fibroblasts.

Materials and Methods

Fibroblast Cultures

Human gingival fibroblasts were taken from frozen samples. Cell cultivation was accomplished in disposable culture flasks (100×20 mm) with 10 ml of Dulbecco's Modified Eagle Medium (DMEM) containing 5% equine serum, penicillin (100 units/ml), streptomycin (100 ug/ml), neomycin (100 units/ml), fungizone (5 ug/ml), anti-PPLO mix (Amphotericin B), and fibronectin at 37° C. in 5% $CO_2$/air.

Sterile, six-well culture plates with fibronectin substrate were seeded with approximately 100,000 cells/ml each and incubated until the pre-confluent monolayer stage was reached. All medium was removed and the cells washed twice with phosphate buffered saline. Incubation was continued for five days with DMEM medium in each of the six wells. Individual wells were assigned as either a specific control or experimental treatment well. The control well contained untreated control cells grown in the DMEM medium without retinoids; the test wells contained filter-sterilized (0.2 u filter) retinoids dissolved in DMEM medium: 200 ng/ml retinoid, 400 ng/ml retinoid, 600 ng/ml retinoid, 800 ng/ml retinoid and 1000 ng/ml retinoid, respectively. Medium was replenished daily.

The retinoids which were used in these studies were provided by Hoffman-La Roche, Inc. and were identified as Ro 4-3780/000 (isotretinoin) and Ro 10-1670/000 (acitretin). In order to ensure that the fibroblasts were viable before the actual tests begin, the dye exclusion test was performed.

Experimental Design

The pre-incubated fibroblast culture was counted to determine the population density. An equal number of fibroblasts (100,000/ml) was assigned into one control group and five treatment groups, in culture wells. The treatment groups contained retinoid concentrations based on the data of Rollman and Vahlquist (1983) noted below:

Group 1 - untreated, control fibroblast culture;
Group 2 - fibroblast culture treated with retinoid only, at concentration of 200 ng/ml;
Group 3 - fibroblast culture treated with retinoid only, at concentration of 400 ng/ml;
Group 4 - fibroblast culture treated with retinoid only, at concentration of 600 ng/ml;
Group 5 - fibroblast culture treated with retinoid only, at concentration of 800 ng/ml;
Group 6 - fibroblast culture treated with retinoid only, at concentration of 1000 ng/ml.

Post-treatment

At the end of the experimental incubation period, each group/well was photographed in vitro by phase microscopy. The culture medium was decanted and the adherent fibroblasts were fixed in situ by absolute methanol.

The fibroblast cultures in each treatment group were stained with Romanofsky stain. The stained fibroblasts were examined under an inverted light microscope. Fibroblast cells in a known grid area in each culture well were counted, and the populations determined. After histological assessment and counting, photomicrographs were taken.

Results and Discussion

Figure 2:
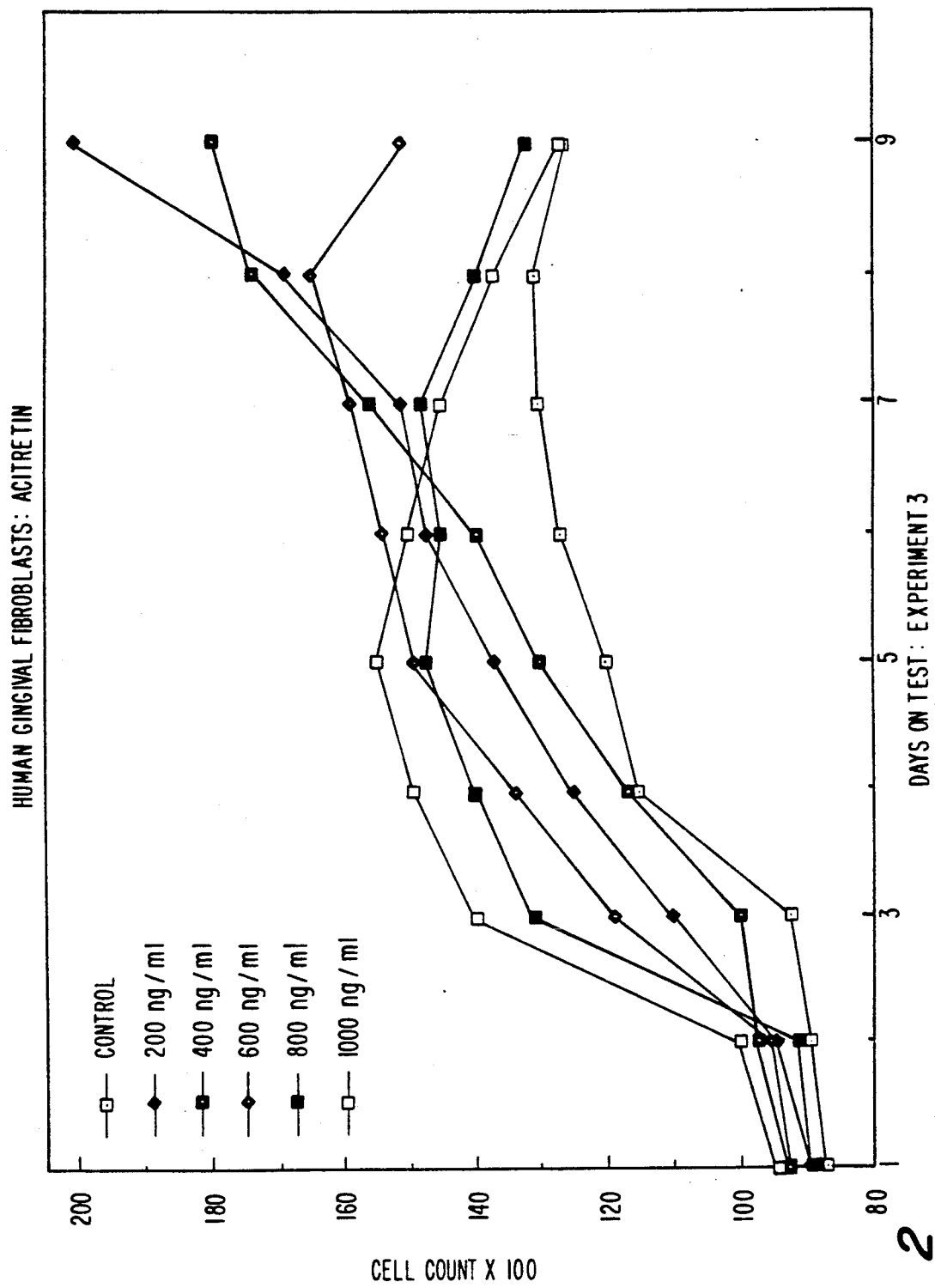
FIG. 2 is a graph showing the number of human gingival fibroblasts counted in six wells of a cell culture plate at one-day intervals over a period of nine days, each of the wells containing either a specified concentration (from 200 to 1000 ng/ml) of acitretin dissolved in culture medium, or none at all (control).

After nine days on test, as shown in FIGS. 1 and 2, all five retinoid concentrations for both isotretinoin and acitretin induced increased fibroblast population growth. After the fifth day, the two higher levels of both retinoids showed lessened growth and a trend returning toward the normal growth curve. In these two retinoid levels, dead and dying cells were noted in the cell culture wells.

The increased gingival fibroblast population growth induced by the retinoids is of significance in treating periodontal disease because of the probable correlation with increased collagen production and resultant connective tissue formation and strengthening.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

1. A method of treating a patient suffering from periodontitis comprising topically administering to an affected periodontal tissue area for an effective period of time an effective periodontal tissue protective amount of a pharmaceutical composition containing at least one retinoid compound selected from the group consisting of Vitamin A aldehyde, Vitamin A esters, etretinate, acitretin, and combinations thereof, wherein said pharmaceutical composition is substantially free of Vitamin A and Vitamin A acid.

2. A method according to claim 1 wherein said composition comprises at least one retinoid compound selected from the group consisting of Vitamin A aldehyde, Vitamin A esters, etretinate, acitretin, and combinations thereof and a pharmaceutically acceptable inert carrier or vehicle, said composition being substantially free of Vitamin A and Vitamin A acid.

3. A method according to claim 1 wherein said composition is a cream, ointment, gel or paste.

4. A method according to claim 3 wherein said composition is in the form of a toothpaste or tooth gel.

5. A method according to claim 1 wherein said composition is in the form of a slow release patch adhered to the periodontal tissues.

6. A method according to claim 1 wherein said composition is a liquid solution of at least one retinoid selected from the group consisting of Vitamin A aldehyde, Vitamin A esters, etretinate, acitretin, and combinations thereof, topically administered through the use of an irrigation device associated with a blunt hypodermic needle, said pharmaceutical composition being substantially free of Vitamin A and Vitamin A acid.

7. A method according to claim 1 wherein said composition is in the form of filaments of food grade plastic incorporating at least one retinoid selected from the group consisting of Vitamin A aldehyde, Vitamin A esters, etretinate, acitretin, and combinations thereof and suitable for insertion in the gingival crevices, said pharmaceutical composition being substantially free of Vitamin A and Vitamin A acid.

8. A method according to claim 1 wherein said composition is in an emulsion of at least one retinoid selected from the group consisting of Vitamin A aldehyde, Vitamin A esters, etretinate, acitretin, and combinations thereof in a sticky vehicle, said pharmaceutical composition being substantially free of Vitamin A and Vitamin A acid.

9. A method according to claim 1 wherein said composition is in the form of a chewing gum.

10. A method according to claim 1 wherein said pharmaceutical composition contains from about 0.01 to about 0.1% weight of at least one retinoid compound selected from the group consisting of Vitamin A aldehyde, Vitamin A esters, etretinate, acitretin, and combinations thereof, said pharmaceutical composition being substantially free of Vitamin A and Vitamin A acid.

11. A method according to claim 10 wherein said pharmaceutical composition contains from about 0.025 to about 0.1% by weight of at least one retinoid compound selected from the group consisting of Vitamin A aldehyde, Vitamin A esters, etretinate, acitretin, and combinations thereof, said pharmaceutical composition being substantially free of Vitamin A and Vitamin A acid.

* * * * *